United States Patent
Shor et al.

(10) Patent No.: US 10,501,720 B2
(45) Date of Patent: *Dec. 10, 2019

(54) MIXING AND FILTERING SYSTEM

(71) Applicant: SANI-TECH WEST, INC., Camarillo, CA (US)

(72) Inventors: Richard J. Shor, Moorpark, CA (US); Chris A. Ballew, Thousand Oaks, CA (US)

(73) Assignee: SANI-TECH WEST, INC., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,737

(22) Filed: Mar. 6, 2019

(65) Prior Publication Data

US 2019/0264165 A1  Aug. 29, 2019

Related U.S. Application Data

(63) Continuation of application No. 14/885,541, filed on Oct. 16, 2015, now Pat. No. 10,260,036.

(Continued)

(51) Int. Cl.
*C12M 1/00* (2006.01)
*C12M 1/26* (2006.01)
(Continued)

(52) U.S. Cl.
CPC .......... *C12M 47/02* (2013.01); *C12M 27/02* (2013.01); *C12M 29/00* (2013.01); *C12M 33/14* (2013.01); *C12M 37/02* (2013.01); *C12M 37/04* (2013.01)

(58) Field of Classification Search
CPC ...... C12M 47/02; C12M 27/02; C12M 29/00; C12M 33/14; C12M 37/02; C12M 37/04
See application file for complete search history.

(56) References Cited

U.S. PATENT DOCUMENTS 2,121,458 A  6/1938  Vogelbusch
2,390,388 A  12/1945  Rector
(Continued)

FOREIGN PATENT DOCUMENTS

CN  202751989  2/2013
CN  103071418  5/2013
(Continued)

OTHER PUBLICATIONS

Carl Roth GmbH+Co. KG—life science chemikalien laborbedarf; Laboratory Glass, Vessels, Consumables/Stirrer reactors/Stirrer reactor sets/1GL 45 stirrer reactors; Duran Group Material Duran; accessed Mar. 13, 2014; 1 page.
(Continued)

*Primary Examiner* — William H. Beisner
*Assistant Examiner* — Danielle B Henkel
(74) *Attorney, Agent, or Firm* — SoCal Law Group LLP; Guy Cumberbatch; Steven C. Sereboff

(57) ABSTRACT

An apparatus for growing and separating cells or micro carriers from fluid medium in an aseptic environment, has a sealed, air and liquid tight, container having a port to allow for the introduction of fluid, gas or components, a filter with a filtration medium mounted centrally around an axis extending through the container, a mixing assembly that rotates around the filtration medium to allow for suspension of media or agitation thereof, and the mixing assembly has vanes containing a magnetic unit in a lower portion thereof that allows for coupling to a stir plate for driving the vanes of the mixing assembly. The vanes are preferably suspended by a central bearing located above the filter, and preferably the vanes extend downward to proximate the bottom of the container to the same extent as the filter and a diptube located along the axis of the filter and vanes.

20 Claims, 11 Drawing Sheets

Related U.S. Application Data

(60) Provisional application No. 62/065,543, filed on Oct. 17, 2014.

(51) Int. Cl.
*C12M 1/06* (2006.01)
*C12M 1/12* (2006.01)

(56) References Cited

U.S. PATENT DOCUMENTS

| | | |
|---|---|---|
| 2,530,814 A | 11/1950 | De Becze et al. |
| 2,556,854 A | 6/1951 | Spears et al. |
| 2,686,754 A | 8/1954 | Monod |
| 2,713,702 A | 7/1955 | Jewell |
| 2,952,588 A | 9/1960 | Rinderer |
| 3,028,476 A | 4/1962 | Hug |
| D200,494 S | 3/1965 | Bezark, Jr. |
| 3,172,235 A | 3/1965 | Bjorklund |
| 3,186,917 A | 6/1965 | Gerhardt et al. |
| 3,209,387 A | 10/1965 | Lukesch |
| 3,216,908 A | 11/1965 | Kratochvil |
| 3,227,557 A | 1/1966 | Ash |
| 3,333,829 A | 8/1967 | Moore et al. |
| 3,572,651 A | 3/1971 | Harker |
| 3,622,129 A | 11/1971 | Mazowski |
| 3,645,508 A | 2/1972 | Balteau |
| 3,647,632 A | 3/1972 | Johnson et al. |
| 3,875,000 A | 4/1975 | Kaneda |
| 3,900,186 A | 8/1975 | Balas |
| 3,966,599 A | 6/1976 | Burkhead |
| 4,025,394 A | 5/1977 | Young |
| 4,178,209 A | 12/1979 | Tolbert et al. |
| 4,184,916 A | 1/1980 | Tolbert et al. |
| 4,204,774 A | 5/1980 | de Bruyne |
| 4,289,854 A | 9/1981 | Tolbert et al. |
| 4,342,835 A | 8/1982 | Hitzman et al. |
| 4,343,904 A | 8/1982 | Birch et al. |
| 4,382,685 A | 5/1983 | Pearson |
| 4,406,786 A | 9/1983 | Hein |
| 4,448,884 A | 5/1984 | Henderson |
| 4,465,377 A | 8/1984 | de Bruyne |
| 4,495,074 A | 1/1985 | Hagiwara |
| 4,512,666 A | 4/1985 | O'Connell |
| 4,535,062 A | 8/1985 | Muller |
| 4,568,192 A | 2/1986 | Kudermann et al. |
| 4,596,779 A | 6/1986 | Ono |
| 4,599,170 A | 7/1986 | Friedman et al. |
| 4,634,675 A | 1/1987 | Freedman et al. |
| 4,639,422 A | 1/1987 | Geimer et al. |
| 4,649,118 A | 3/1987 | Anderson |
| 4,727,040 A | 2/1988 | Freedman et al. |
| 4,773,997 A | 9/1988 | Butte |
| 4,833,083 A | 5/1989 | Saxena |
| 4,839,046 A | 6/1989 | Chandler |
| 4,882,062 A | 11/1989 | Moeller et al. |
| 4,888,294 A | 12/1989 | Van Wezel et al. |
| 4,906,577 A | 3/1990 | Armstrong et al. |
| 4,921,792 A | 5/1990 | Trawinski et al. |
| 4,988,623 A | 1/1991 | Schwarz et al. |
| 5,002,890 A | 3/1991 | Morrison |
| 5,008,197 A | 4/1991 | Wergeland et al. |
| 5,019,512 A | 5/1991 | Varecka et al. |
| 5,032,524 A | 7/1991 | Buntemeyer et al. |
| 5,079,161 A | 1/1992 | Mitsuda et al. |
| 5,081,036 A | 1/1992 | Familletti |
| 5,096,814 A | 3/1992 | Aivasidis et al. |
| 5,100,799 A | 3/1992 | Mundt |
| 5,126,269 A | 6/1992 | Fike et al. |
| 5,155,035 A | 10/1992 | Schwarz et al. |
| 5,240,322 A | 8/1993 | Haber et al. |
| 5,246,855 A | 9/1993 | Katinger et al. |
| 5,267,791 A | 12/1993 | Christian et al. |
| 5,270,207 A | 12/1993 | Matsumura et al. |
| 5,342,781 A | 8/1994 | Su |
| 5,366,632 A | 11/1994 | Balsimo et al. |
| 5,501,971 A | 3/1996 | Freedman et al. |
| 5,622,819 A | 4/1997 | Herman |
| 5,630,706 A | 5/1997 | Yang |
| 5,637,496 A | 6/1997 | Thaler |
| 5,664,938 A | 9/1997 | Yang |
| 5,672,481 A | 9/1997 | Minshall et al. |
| 5,846,828 A | 12/1998 | Peterson et al. |
| 6,382,827 B1 | 5/2002 | Gebrian |
| 6,464,387 B1 | 10/2002 | Stogsdill |
| 6,593,128 B1 | 7/2003 | Kiy et al. |
| 6,783,740 B2 | 8/2004 | Colby et al. |
| 6,837,613 B2 | 1/2005 | Terentiev |
| 6,844,186 B2 | 1/2005 | Carll |
| 7,011,852 B2 | 3/2006 | Sukavaneshvar et al. |
| 7,611,891 B2 | 11/2009 | Sundberg |
| 7,735,658 B2 | 6/2010 | Hidaka et al. |
| 7,789,552 B2 | 9/2010 | Girvin et al. |
| 8,057,092 B2 | 11/2011 | Ryan et al. |
| 8,123,395 B2 | 2/2012 | Baumfalk et al. |
| 8,147,737 B2 | 4/2012 | Nasu et al. |
| 8,182,137 B2 | 5/2012 | Terentiev |
| 8,337,074 B2 | 12/2012 | Wild et al. |
| 8,337,780 B2 | 12/2012 | Gaskins et al. |
| 8,363,222 B2 | 1/2013 | Girvin et al. |
| 8,366,311 B2 | 2/2013 | Vanhamel et al. |
| 10,260,036 B2 * | 4/2019 | Shor .............. C12M 33/14 |
| 2002/0154570 A1 | 10/2002 | Gebrian |
| 2009/0027997 A1 | 1/2009 | Meier |
| 2009/0130757 A1 | 5/2009 | Terentiev |
| 2009/0323466 A1 | 12/2009 | Vanhamel |
| 2010/0015696 A1 | 1/2010 | Claes et al. |
| 2010/0290308 A1 | 11/2010 | Terentiev |
| 2010/0304473 A1 | 12/2010 | Kim et al. |
| 2011/0038222 A1 | 2/2011 | Ludwig et al. |
| 2011/0117639 A1 | 5/2011 | Suazo et al. |
| 2011/0297861 A1 | 12/2011 | Cronin et al. |
| 2011/0318814 A1 | 12/2011 | Kshirsagar et al. |
| 2016/0355774 A1 | 12/2016 | Konishi et al. |

FOREIGN PATENT DOCUMENTS

| | | |
|---|---|---|
| CN | 203030232 | 7/2013 |
| CN | 203123598 | 8/2013 |
| CN | 203124004 | 8/2013 |
| CN | 203183963 | 9/2013 |
| CN | 203196580 | 9/2013 |
| EP | 0242984 A1 | 10/1987 |
| EP | 0127971 B1 | 10/1990 |
| EP | 1398072 A1 | 3/2004 |
| EP | 1516920 A1 | 3/2005 |
| EP | 2133139 B1 | 4/2012 |
| WO | 2015122528 A1 | 8/2015 |

OTHER PUBLICATIONS

Wenk Lab Tec.com; GL45 Stirred Reactor, Folding magnetic stirrer for GL45 stirred reactor, incl. s, Price on request; Folding magnetic stirrer for GL45 stirred reactor, incl. s; accessed Mar. 12, 2014; 1 page.

Extended European Search Report dated Mar. 19, 2018 for European application No. 15850679.0.

* cited by examiner

MIXING AND FILTERING SYSTEM

RELATED APPLICATION INFORMATION

This application is a continuation of U.S. patent application Ser. No. 14/885,541, filed Oct. 16, 2015, now issued as U.S. Pat. No. 10,260,036, which claims priority from U.S. Provisional Patent Application Ser. No. 62/065,543, filed Oct. 17, 2014, the disclosures of which are hereby incorporated by reference in its entirety

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

The present invention relates to mixing and filtering systems such as for separating cells from a fluid medium or for separating cells from micro carriers suspended in a fluid medium.

Description of the Related Art

In the field of culturing cells for biological and/or chemical use or testing and/or other reasons, cells are grown in a culture fluid or on micro carriers suspended in a fluid medium. The cells must then be separated from debris such as dead cells and/or from the micro carriers. An aseptic mixing and filtering system is used to isolate healthy cells. These cells may be used for many purposes, for example for vaccines, for testing for vaccines, for testing for viruses, enzymes, synthetic hormones, and other products of biotechnology.

The cells are separated by putting a culture with cells and/or cells on micro carriers into an aseptic tank with a mixing and filtering system. When separating cells from a fluid medium or from micro carriers suspended in a fluid medium, it is important to achieve complete mixing and filtering or as complete as possible to obtain the highest concentration of cells. It is also important not to mix too harshly, so that cells do not get damaged. Further, it is important to use equipment that is inert and that is easily cleaned and sterilized so the aseptic environment may be maintained. The presence of dead cells and/or unhealthy cells (generally smaller than healthy cells) can substantially hinder and slow down the process of achieving a concentration of fresh, healthy cells for maximum biological effectiveness.

Many mixing and filtering systems can leave a lot of healthy cells unfiltered and/or let too much debris stay with the healthy cells. Mixing and filtering systems can also be difficult to place inside a hermetically sealed vessel or container without comprising the aseptic environment.

The mixing and filtering system normally includes a vessel or container, a tube usually inserted through an opening at the top of the vessel (e.g., through a sealing cap of the vessel), a filter assembly and a mixing assembly. The tube forms a diptube used to remove debris or to remove healthy cells, depending on which is being filtered out of the medium. Therefore, the tube will normally have an opening as close to the bottom of the vessel as possible however it will remain contained behind the barrier of the filter assembly.

Mixing assemblies may have an external drive and a mechanical coupling. However, in such case, the vessel cannot be truly aseptic. A type of mixing assembly that provides internal drive and is therefore aseptic is a magnetic stirrer or mixer. There is a magnet or magnets in the form of a stir bar or other magnetic arrangement inside the vessel. A magnetic stir plate is located outside of the vessel but as close as possible to the magnet(s) inside the vessel. The stir plate has a movable or changeable magnetic field that attracts and repels the magnet(s) inside the vessel in such a way that the magnet(s) inside the vessel rotate(s).

Several U.S. patents are examples of using magnetic mixing in a mixing and filtering system in a vessel. U.S. Pat. No. 4,639,422 to Geimer discloses a mixing vessel having a central tube, vanes and magnetic mixing where the magnet is located below the bottom of the vanes. The vanes appear to be located inside the outer diameter of a filter.

U.S. Pat. No. 4,649,118 to Anderson discloses a mixing device with a central magnet.

U.S. Pat. No. 5,126,269 to Fike et al, U.S. Pat. No. 3,647,632 to Johnson et al, and U.S. Pat. Nos. 4,184,916 and 4,289,854 to Tolbert all disclose a mixing device using a stir bar.

U.S. Pat. No. 6,593,128 to Kiy et al discloses a magnetic mixing device with a magnetic follower.

SUMMARY OF THE INVENTION

According to exemplary embodiments, an apparatus is provided for growing and separating cells or micro carriers from fluid medium in an aseptic environment. The apparatus has a sealed, air and liquid tight, container having a port to allow for the introduction of fluid, gas or components, a filter with a filtration medium mounted centrally around an axis extending through the container, a mixing assembly that rotates around the filtration medium to allow for suspension of media or agitation thereof, and the mixing assembly has vanes containing a magnetic unit in a lower portion thereof that allows for coupling to a stir plate for driving the vanes of the mixing assembly. The vanes are preferably suspended by a central bearing located above the filter, and preferably the vanes extend downward to proximate the bottom of the container to the same extent as the filter and a diptube located along the axis of the filter and vanes.

DETAILED DESCRIPTION

Figure 1:
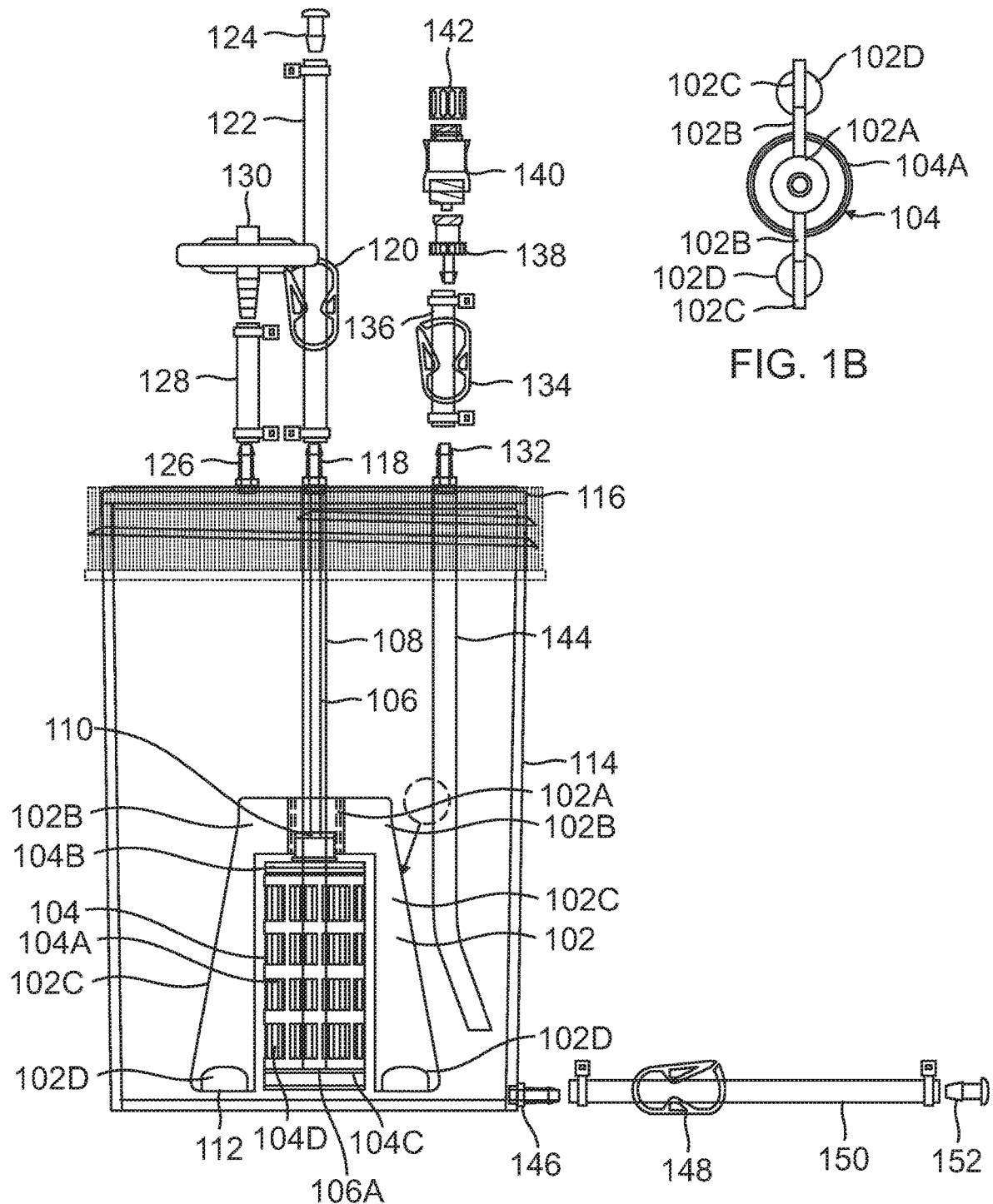
FIGS. 1A and 1B are schematic diagrams of a mixing and filtering system, according to an embodiment.

In various embodiments, the system provides a mechanism for mixing and filtering fluids in a vessel. For example, the system may be used to separate cells from a fluid medium, or to separate cells from micro carriers suspended in a fluid medium. The micro carriers may be glass and/or plastic particles, beads, and/or other structures.

In various embodiments, the system may be used to agitate fluids without any cells or particles, cells suspended in fluids with or without particles, glass and/or plastic particles, beads, and/or micro carriers and to draw fluid along with the separated cells out of the mixture. The system may include various features that enable greater effectiveness at retrieving cell mixtures over the prior art, such as a vertically extending fin that moves around a lateral face of a cylindrical filter unit, and/or a central support unit with an opening disposed to acquire residual fluid. In a most preferred embodiment, the fin or fin (or wings or mixing blades) are supported on a bearing on a centrally positioned support unit at a point above a filter unit, which filter unit is also supported on the support unit. The fin or fins extend outward from proximate the bearing and extend downward for the length or substantially the length of the filter unit. A magnetic device is positioned and supported in the bottom portion of the fin or fins. Therefore, the filter, the fins, and a central diptube through the filter may all extend downward in the container to the same or approximately the same clearance from the bottom of the container to best retrieve cells or debris or other material being removed from the container. The fins may extend radially outward from the filter and extend further out near the bottom of the filter than at the top. These aspects of the most preferred embodiment may each be used individually or in any combination desired in lesser preferred embodiments.

The system may include a mix unit that includes one, two, or more wings or other structures that are configured to extend laterally from a bearing having a vertical opening that permits the support unit to extend through the middle of the bearing. The bottom of each wing or other structure may include a magnet that is disposed between the center of the container and the outer lateral walls of the container. The wings may form a split delta form that is divided by a bearing, i.e., each wing may be shaped somewhat like one side of the Greek capital letter delta split vertically through the middle. This shape may also be described as an elongate scalene right triangle with its shortest side at the bottom and its side opposite that vertically oriented and radially inwardly disposed. The split delta is preferred, however, other wing shapes, preferably extending a vertical length or substantially a vertical length of the filter.

The support unit may include a passage that extends through the length of the support unit for a diptube to extend therethrough, and a separation unit may be attached to the support unit.

The separation unit may include a filter and/or screen, and the separation unit may extend down to the bottom of a container. The separation unit may be close to or abutted against the bottom inner surface of the container, and may cover the bottom center of the container.

In some embodiments, the wings of the mix unit may be configured to rotate around the separation unit without traveling underneath the separation unit. Similarly, in some embodiments, the magnetic device is not located below the filter, and therefore the filter and/or the diptube and/or the wings may get as close to the bottom of the container as possible.

These and/or other features may provide advantages over the prior art with respect to mixing and filtering effectiveness, product recovery, durability, speed, and/or ease/cost of manufacture.

Advantages of at least some of the embodiments disclosed include obtaining good mixing of fluid that is located proximate a bottom of the vessel and/or stirring fluid for a depth of a filter, and stirring fluid proximate the filter.

Features of various embodiments are described in greater detail below in connection with the figures.

II. Figure Descriptions

A. FIG. 1

FIGS. 1A and 1B are schematic diagrams of a mixing and filtering system, according to an embodiment. As shown, FIG. 1 includes: a mix unit 102, a separation unit 104, a support unit, diptube 106, a support unit 108, a support unit bearing 110, a pair of magnets 112, a container 114, a container lid 116, a first port 118, a first clamp 120, a first tube 122, a first plug 124, a second port 126, a second tube 128, a first vent filter 130, a third port 132, a second clamp 134, a third tube 136 (or pipe), a barb 138, a swabable valve 140, a cap 142, an angled pipe 144, a fourth port 146, a third clamp 148, a fourth pipe 150, a second plug 152, a grip section 102A, a pair of first mix sections 102B, a pair of second mix sections 102C, a pair of magnet housings 102D, an outer wall 104A, a cap 104B, an end 104C, and a filter 104D.

The system may be used within a container 114 that has a container lid 116.

The support unit 108 may be suspended from the container lid 116 and/or from other locations, such as above the container lid 116. The support unit 108 may define a passage through its center that opens at the top and bottom of the support unit 108 so that diptube 106 may pass therethrough.

In various embodiments, a lower opening 106A of the diptube 106 may be formed at or near the bottom of the container or as proximate thereto as possible, and may open downward, laterally, and/or upward. In the embodiment shown, the diptube 106 permits fluid communication between the interior of the separation unit 104 and the first port 118.

The support unit 108 may extend through a central opening of the support unit bearing 110, and may be attached to the bearing through friction, adhesive bonding, or a mechanical attachment such as screws.

The support unit 108 may extend downward from the support unit bearing 110 into a central cavity of the separation unit 104. The separation unit 104 may include the outer wall 104A, the cap 104B, the end 104C, and/or the end 104C. The end 104C may be a flat wall without openings, a wall formed with openings, a screen or filter 104D, or an alternate structure. A bottom of the support unit 108 may extend downward until it almost touches the end 104C, or it may abut against or be inserted the end 104C. The lower opening 106A of the diptube 106 may open near or adjacent to the end 104C, or may open into the end 104C where the end 104C includes passages with other openings for permitting fluid communication with the interior of the separation unit 104. The outer wall 104A may form a cylindrical boundary between the cap 104B and the end 104C.

Between the opening at the lower end of the diptube 106 and the area of the container 114 that is outside the separation unit 104, the filter 104D, screen, or other separation mechanism may be installed on the separation unit 104. The filter 104D, screen, or other separation mechanism may be held in place and/or attached to one or more of the outer wall 104A, the cap 104B, and the end 104C. In the embodiment shown in FIG. 1, the filter 104D is a pleated filter that encircles the lateral sides of the support unit 108 within the separation unit 104. In some embodiments, one or more of the outer wall 104A, the cap 104B, and the end 104C may be formed in whole or in part by the filter 104D, the screen, or other separation mechanism.

The bottom of the separation unit 104 may be abutted against and/or placed adjacent to an interior surface of the container 114. In some embodiments, the bottom of the separation unit 104 may be a flat plane that extends parallel to a bottom interior surface of the container 114, and may be within 0.0 inches to 0.2 inches away from the bottom interior surface.

In various embodiments, the mix unit 102 may be rotatably attached to the support unit 108 using the support unit bearing 110. The mix unit 102 may include the grip section 102A, the pair of first mix sections 102B, the pair of second mix sections 102C, the pair of magnet housings 102D, and the pair of magnets 112. In other embodiments, the mix unit 102 may include fewer or more quantities of first mix sections 102B, second mix sections 102C, magnet housings 102D, and magnets 112 (e.g., 1, 3, 4, or 10 of each).

In various embodiments, the grip section 102A may be formed as a ring with a central opening that permits insertion of the support unit bearing 110.

For each side of the mix unit 102 having subcomponents (e.g., 102A, 102B, 102C, and/or 102D), the first mix section 102B may be attached to and/or integrally formed with the grip section 102A. The first mix section 102B may have a shape formed as a flat wall with two parallel faces that are parallel to a plane extending radially away from the grip section 102A. The upper edge and the lower edge of the first mix section 102B may be flat and extend radially away from the grip section 102A.

The first mix section 102B may be divided into an upper part and a lower part. The upper part may include the upper edge, and may have a distal edge to the grip section 102A that extend downward parallel to the support unit 108. The lower part may have a distal edge distal to the grip section 102A that extends downward and laterally away from the grip section 102A such that the top of the lower part's distal edge is closer to the grip section 102A than the bottom of the lower part's distal edge. The lower edge of the lower part may be divided into a first section that is proximate to the grip section 102A, and a second section that is distal to the grip section 102A. The first section may extend over the separation unit 104 such that a projection of the first section downward parallel to the support unit 108 would intersect with the separation unit 104. The second section may be the point of attachment between the first mix section 102B and the second mix section 102C.

For each side of the mix unit 102 having subcomponents (e.g., 102A, 102B, 102C, and/or 102D), a second mix section 102C may be attached to and/or integrally formed with the first mix section 102B, and may extend downward from the first mix section 102B. The second mix section 102C may have a shape formed as a flat wall with two parallel faces that are parallel to a plane extending radially away from the grip section 102A.

The shape of the second mix section 102C may include an upper edge, a proximal edge, a distal edge, and a bottom edge. The upper edge may be integrally formed with and/or attached to the second section of the lower part of the first mix section 102B. The distal edge may extend downward and laterally away from the separation unit 108 such that the upper part of the distal edge is closer to the separation unit 108 than the bottom part of the distal edge, and such that the width of the second mix section 102C as measured in a radial direction is narrower at the top than at the bottom of the second mix section 102C. The upper edge and bottom edge may extend radially away from the support unit 108. The bottom edge may be disposed between 0.01 inches and 0.2 inches from the bottom interior surface of the container 114.

The proximal edge may extend downward from the top of the second mix section 102C parallel and adjacent to the outer wall 104A of the separation unit 104. The proximal edge may be disposed within 0.1 inches and 0.3 inches away from the outer wall 104A.

The magnet housing 102D may be attached to and/or integrally formed with the second mix section 102C, and may extend from both front and back faces of the second mix section 102C perpendicular to a plane extending radially away from the grip section 102A. The magnet housing 102D may define a cavity configured to hold one of the magnets 112 (e.g., a permanent magnet, an electromagnet, etc.). The cavity may open downwards, laterally, closed with a cover, and/or may be integrally formed around the corresponding magnet 112.

During operation, magnets 112 are magnetically engaged with a magnetic mix plate disposed outside the container 114. The magnetic mix plate may drive rotation of the mix unit 102 around the separation unit 104 and/or the support unit 108. Such a magnetic mix plate is a well-known device for magnetic mixing, such as a Heidolph MR Hei-Mix S made by Heidolph North America of Elk Grove Village, Ill. Such magnetic mixing plates may be heated or unheated. (A mixing plate 413 is shown schematically in FIG. 4A, and may be used in any embodiment herein.)

In the embodiment shown in FIG. 1, the sides of the mix unit 102 having subcomponents (e.g., the grip section 102A, the pair of first mix sections 102B, the pair of second mix sections 102C, the pair of magnet housings 102D) are oppositely disposed (e.g. 180 degrees apart). In other embodiments, the sides may be offset at various angles (e.g., 90 degrees, 45 degrees, 60 degrees, etc.). In other words, for embodiments where the sides of the mix unit 102 are in the form of vertically aligned fins, the fins may be offset by varying degree angles around the separation unit 104.

The configuration of one or more of the components of the mix unit 102, the components of the separation unit 104, and/or the components of the container 114 described above may encourage better turbulent mixing and/or fluid vortex formation such that particles bearing cell cultures are more effectively circulated and/or dislodged from the outer surfaces of the separation unit 104. In this way, faster and more effective removal and filtering of cell cultures from micro beads and/or particles formed from glass, plastic, or other materials may be achieved, which may result in higher yields.

For example, the wider bottom portions of the second mix sections 102C (e.g., wider than the top of the first mix sections 102B, extending farther in a lateral direction from a center axis of the separation unit 104) may drive lateral fluid flow away from the separation unit 104 near the bottom of the container 114. This may help generate a toroid-shaped fluid flow within the container 114 that can assist with better mixing. The shape (e.g., as discussed on pages 5-7 and/or as shown in FIG. 1A) of the first mix section 102B and second mix section 102C may also encourage rotational fluid flow and/or vortex shedding that causes particles to be dislodged from the screen, filter 104D, and/or outer wall 104A of the separation unit 104.

The third port 132, the second clamp 134, the third pipe 136, the barb 138, the swabable valve 140, the cap 142, and the angled pipe 144 may be used to introduce additional fluid and/or particles carrying cells or other materials to the container 114.

The fourth port 146, the third clamp 148, the fourth pipe 150, and the second plug 152 may be used to remove or add fluid and/or particles.

The first port 118, the first clamp 120, the first tube 122, and the first plug 124 may permit removal of filtered fluid and/or cells suspended in fluid from the container 114. The first port 118 may be attached to the support unit 108, such as by being inserted within the support unit passage 106. The first clamp 120 may control fluid flow through the first tube 122, and the first plug 124 may provide additional restriction on fluid flow through the first tube 122 by being inserted in the first tube.

In a simple version, there may be only one port, e.g., at the top of the vessel, support unit 108 including passage 106, the filter assembly, and the magnetic mixing assembly. In some embodiments, a filter may not be needed.

B. FIG. 2

Figure 2:
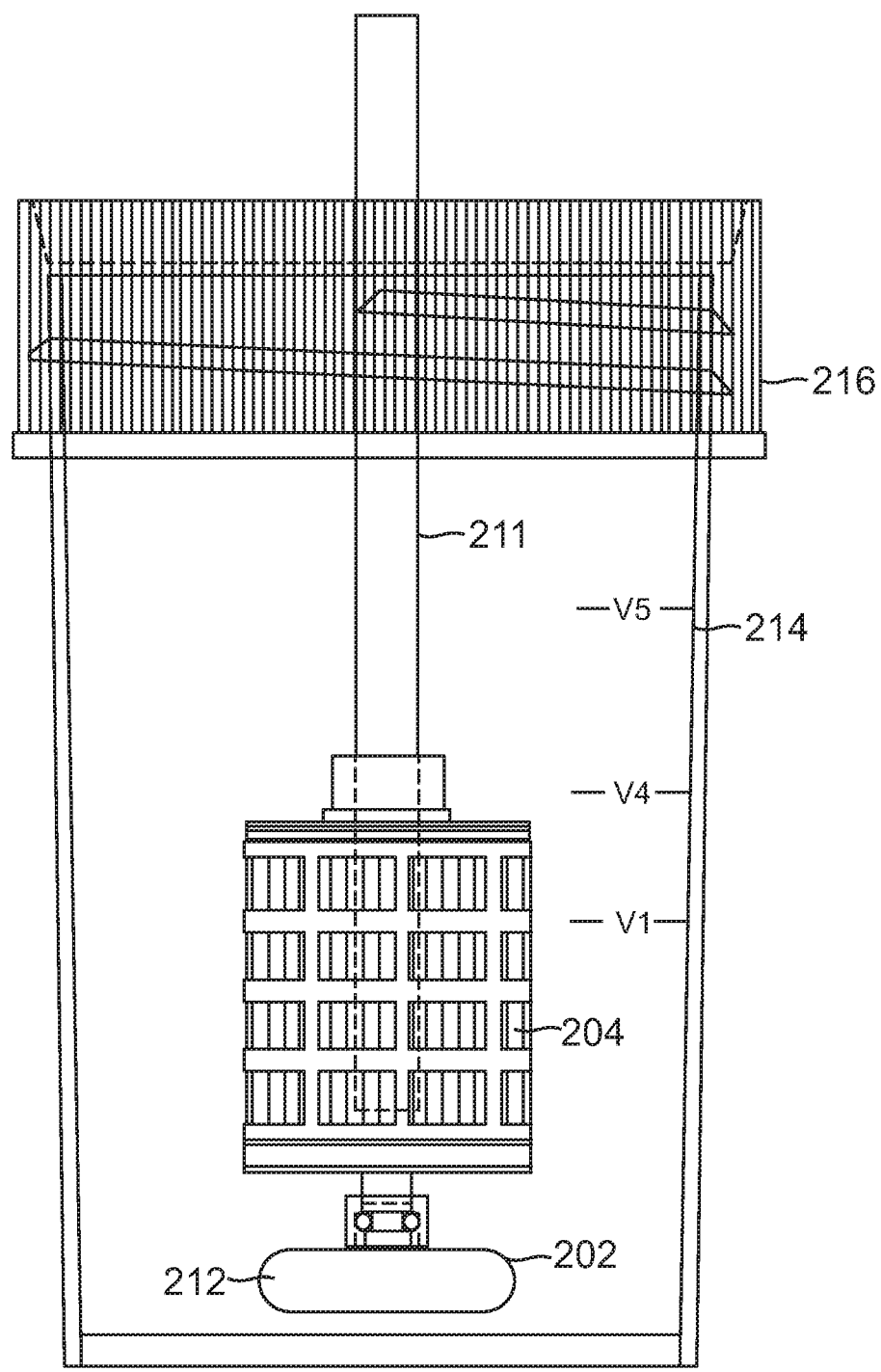
FIGS. 2, 3A, 3B, 4A, 4B, 5A, 5B, and 6 are schematic diagrams of other various embodiments of mixing and filtering systems.

FIG. 2 illustrates an embodiment that includes a mix unit 202, a separation unit 204, a magnet 212, a container 214, and a container lid 216. In the embodiment of FIG. 2, the mix unit 202 includes the magnet 212 in the form of a stir bar that rotates beneath the separation unit 204. There may also be a support unit 211 like support unit 108, which provides a place for a diptube like diptube 106 inside. The diptube preferably extends down to the bottom of the filter, and may have holes in it along its length, including at the bottom, as in some or all other embodiments herein.

Figure 3A:
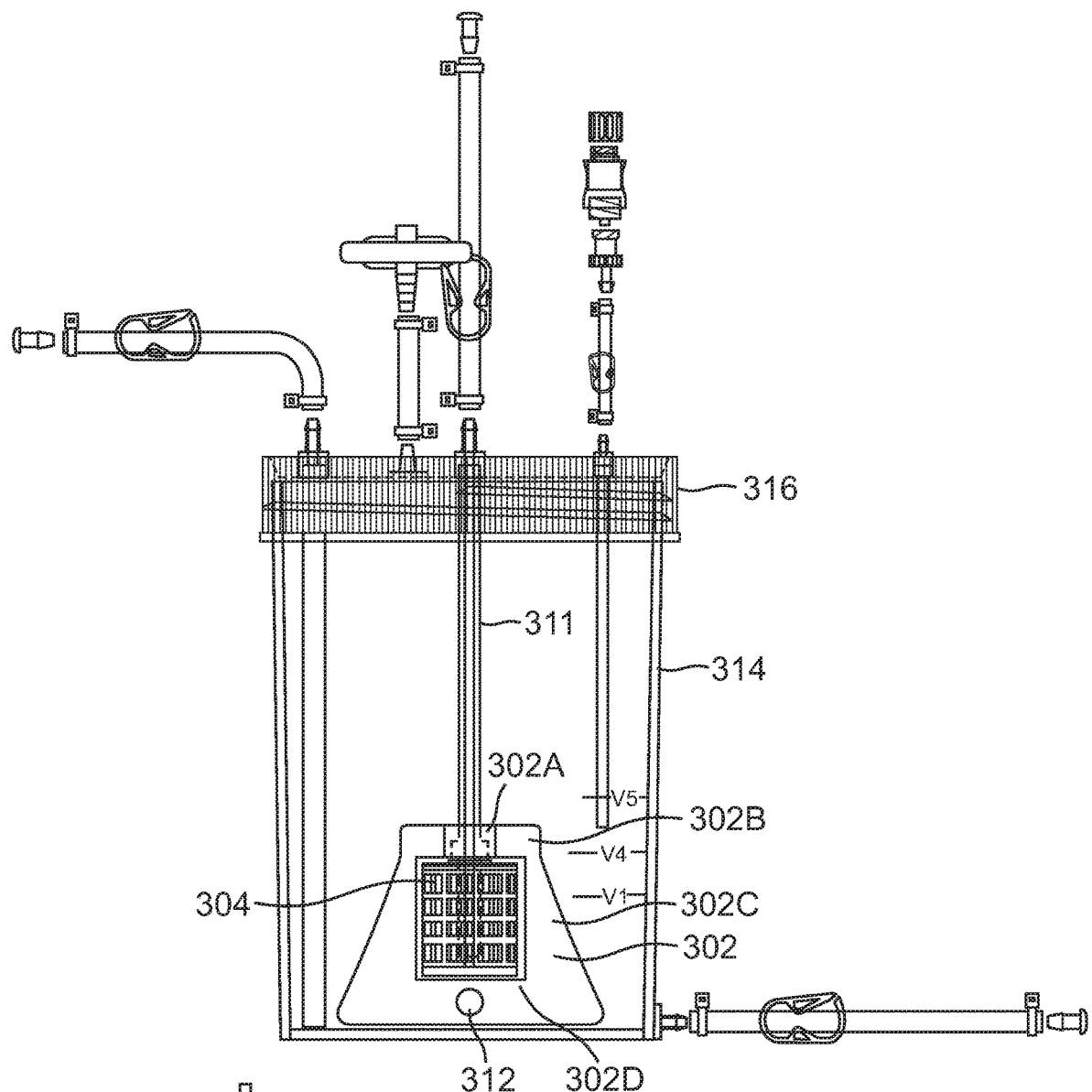
Figure 3B:
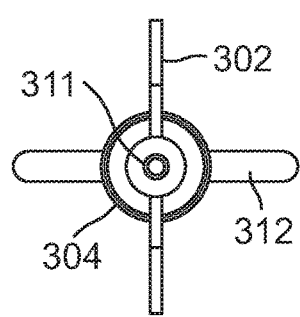

C. FIGS. 3A and 3B

FIGS. 3A and 3B illustrate an embodiment that includes a mix unit 302, a separation unit 304, a magnet 312, a container 314, a container lid 316, a grip section 302A, a pair of first mix sections 302B, a pair of second mix sections 302C, and a magnet housing 302D. FIG. 3A illustrates a side view of the embodiment, and FIG. 3B illustrates a top view of the embodiment.

In the embodiment of FIGS. 3A and 3B, the magnet housing 302D extends laterally below the mix unit 302 and the separation unit 304. The magnet housing 302D is formed as a flat wall with two parallel faces that are parallel to a plane extending radially away from the grip section 302A. The magnet 312 is a stir bar that extends perpendicularly from the parallel faces of the magnet housing 302D.

There may also be a support unit 311 like support unit 108, which provides a place for a diptube like diptube 106 inside. The diptube preferably extends down to the bottom of the filter, and may have holes in it along its length, including at the bottom, as in some or all other embodiments herein.

Figures 4A, 4B:
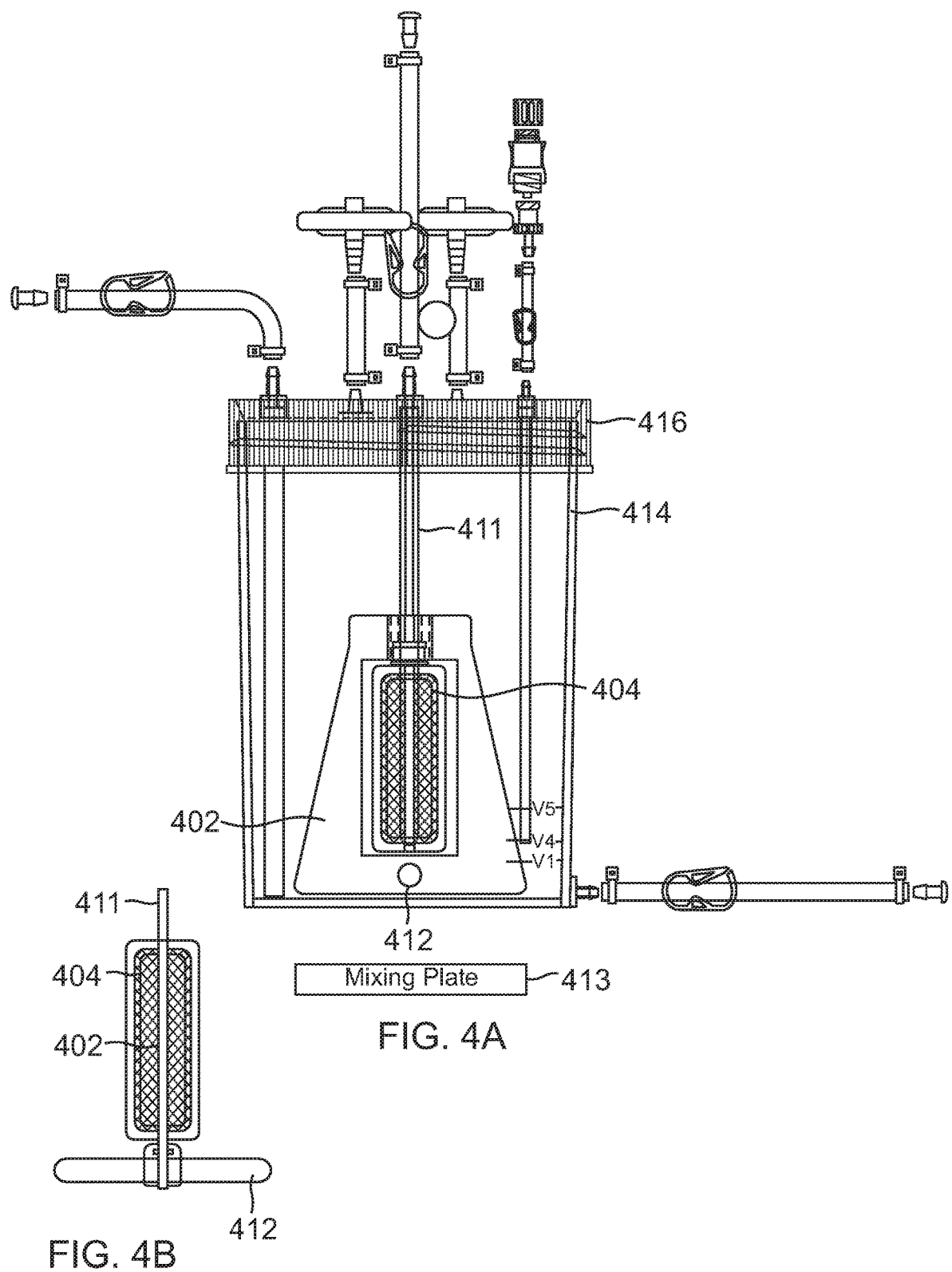

D. FIGS. 4A and 4B

FIGS. 4A and 4B illustrate an embodiment that includes a mix unit 402, a separation unit 404, a magnet 412, a container 414, and a container lid 416. FIG. 4A illustrates a side view of the embodiment, and FIG. 4B illustrates another side view of the mix unit 402 and the separation unit 404 that has been rotated 90 degrees. In the embodiment of FIGS. 4A and 4B, a double bag is used for gamma irradiation. The magnet 412 is a stir bar.

There may also be a support unit 411 like support unit 108, which provides a place for a diptube like diptube 106 inside. The diptube preferably extends down to the bottom of the filter, and may have holes in it along its length, including at the bottom, as in some or all other embodiments herein.

Figure 5A:
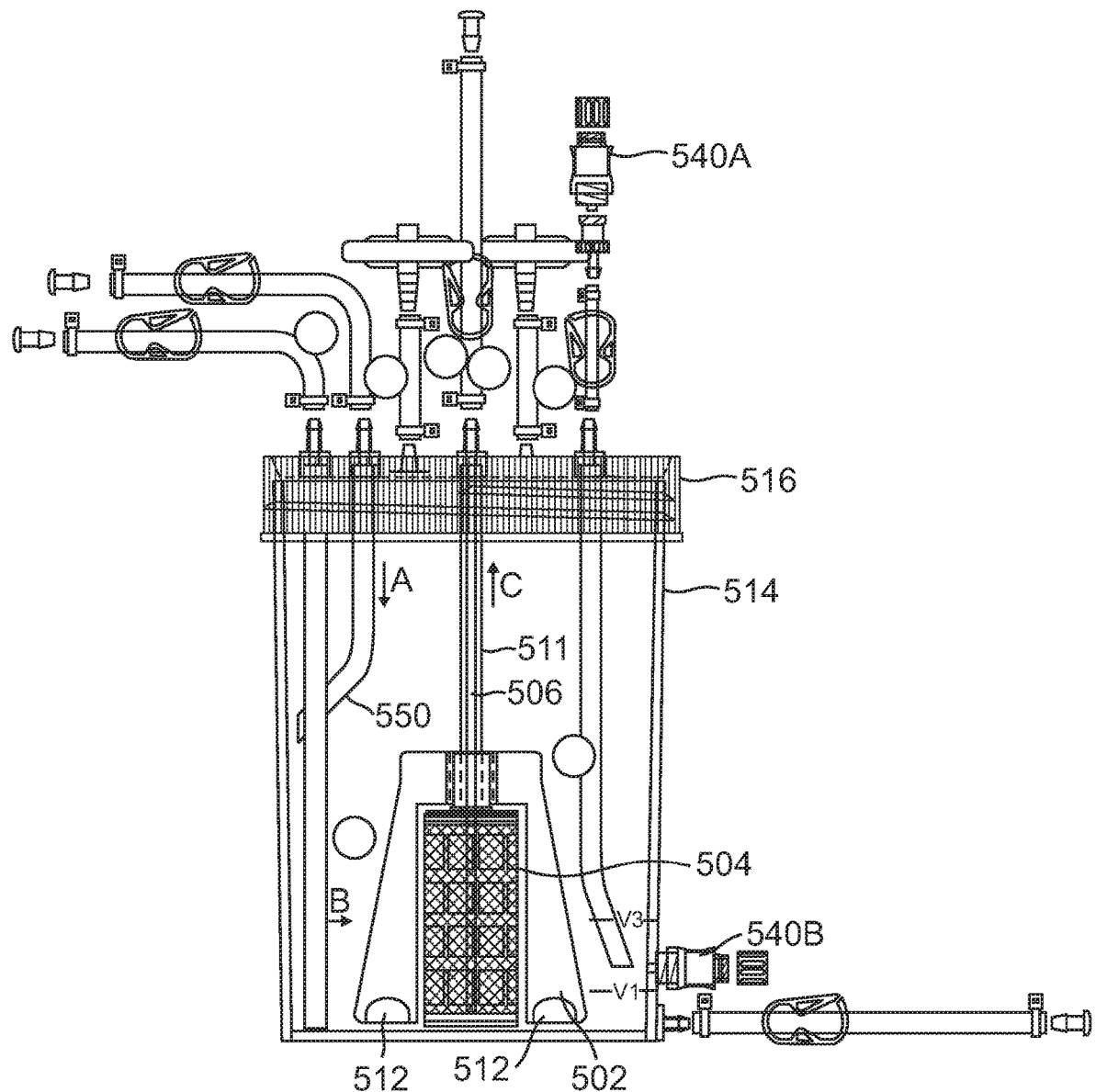
Figure 5B:
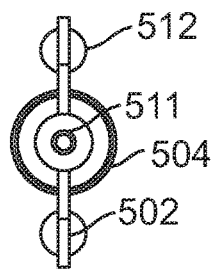

E. FIGS. 5A and 5B

FIGS. 5A and 5B illustrate an embodiment that includes a mix unit 502, a separation unit 504, magnets 512, a container 514, a container lid 516, an upper swabable valve 540A, and a lower swabable valve 540B. FIG. 5A illustrates a side view of the embodiment, and FIG. 5B illustrates a top view of the embodiment.

In the embodiment of FIGS. 5A and 5B, a screen is used in the separation unit 504 without a pleated filter.

A small plug unit referred to as a swabable valve (e.g., upper swabable valve 540A and/or lower swabable valve 540B) is installed onto the vessel to be used as an aseptic sampling method of the product inside the vessel.

There may also be a support unit 511 like support unit 108, which provides a place for a diptube like diptube 106 inside. The diptube preferably extends down to the bottom of the filter, and may have holes in it along its length, including at the bottom, as in some or all other embodiments herein.

F. FIG. 6

Figure 6:
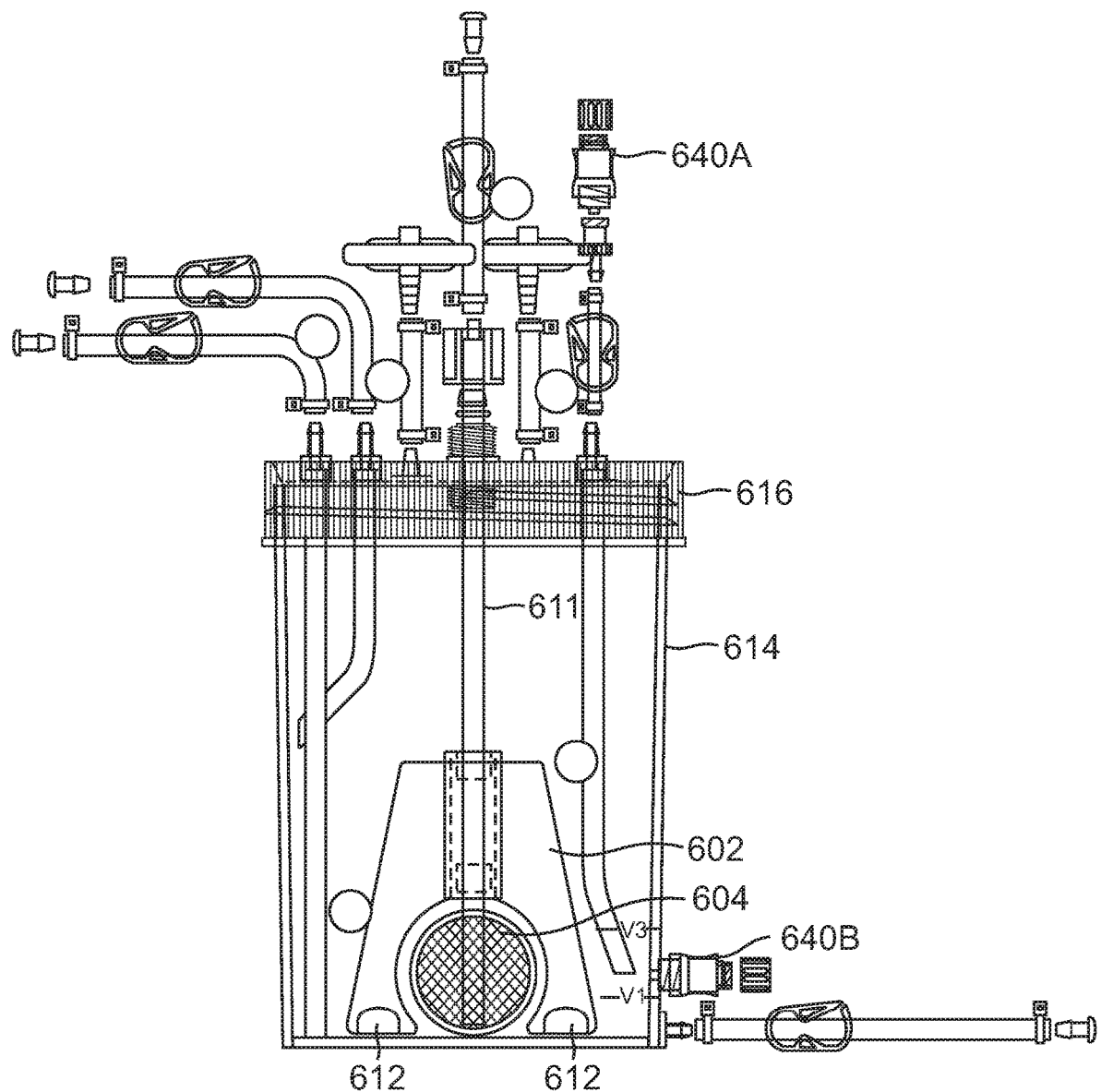

FIG. 6 illustrates an embodiment that includes a mix unit 602, a separation unit 604, magnets 612, a container 614, a container lid 616, an upper swabable valve 640A, and a lower swabable valve 640B.

In the embodiment of FIG. 6, the separation unit 604 may be curved rather than cylindrical, and may be partially or wholly formed as a sphere. The portions of the mix unit 602 that are adjacent to the separation unit 604 may be curved to conform to the shape of the separation unit 602.

A small plug unit referred to as a swabable valve (e.g., upper swabable valve 640A and/or lower swabable valve 640B) is installed onto the vessel to be used as an aseptic sampling method of the product inside the vessel.

There may also be a support unit 611 like support unit 108, which provides a place for a diptube like diptube 106 inside. The diptube preferably extends down to the bottom of the filter, and may have holes in it along its length, including at the bottom, as in some or all other embodiments herein.

Figure 7:
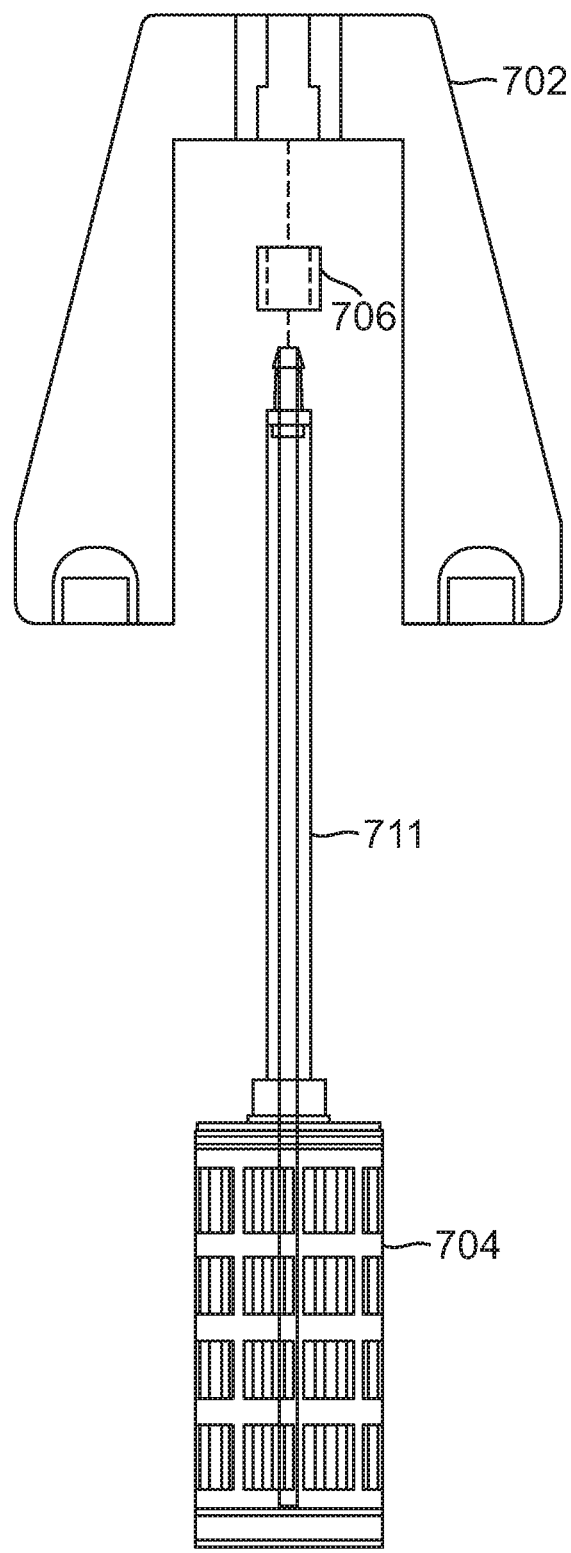
FIG. 7 is an exploded view of components of a mixing and filtering system, according to an embodiment.
Figure 8:
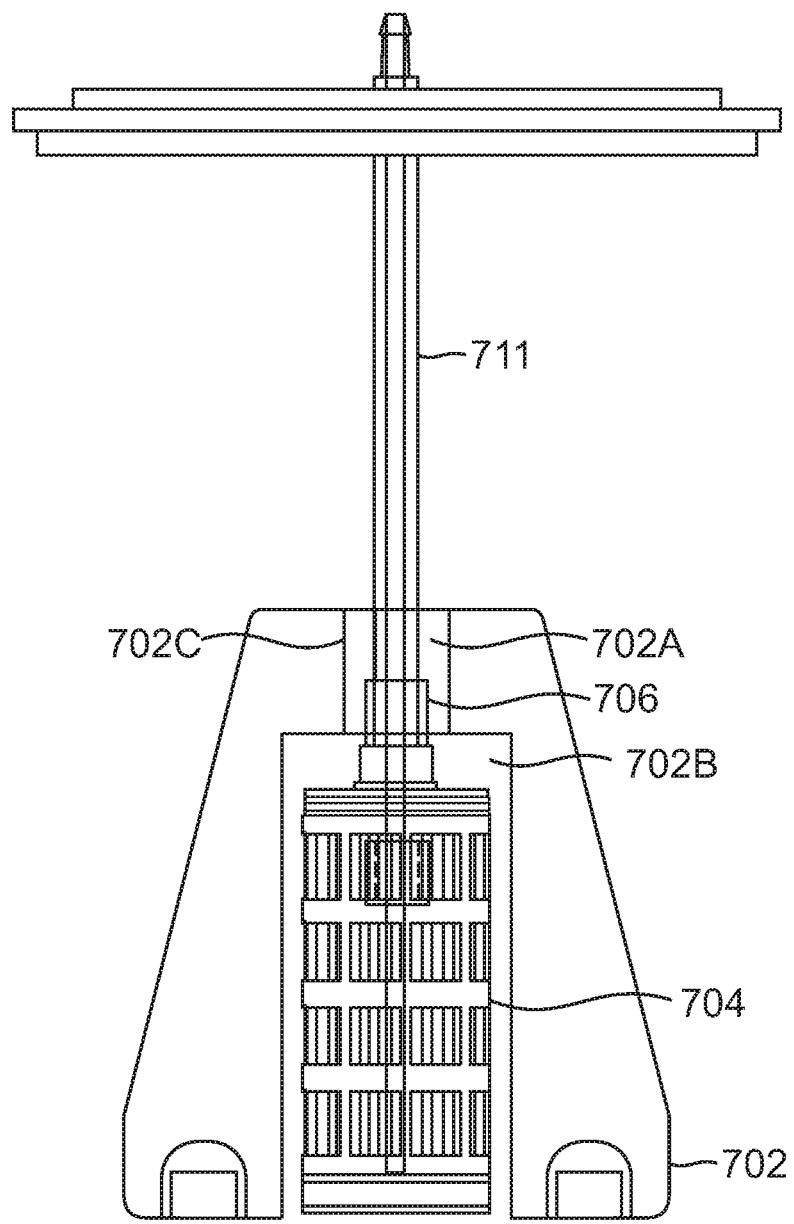
FIG. 8 is an assembled view of components of a mixing and filtering system, according to an embodiment.

G. FIGS. 7 and 8

FIG. 7 is an exploded view of components of a mixing and filtering system, according to an embodiment. FIG. 7 illustrates how a mix unit 702 and a separation unit 704 (filter unit) can be assembled together using a bearing 706 that encircles a support unit. When the mixing and filtering system is assembled, the support unit 711 (like support 108) extends up and through the separation unit, the bearing, and the mix unit. Support unit 711, like support unit 108, provides a place for a diptube like diptube 106 inside. The diptube preferably extends down to the bottom of the filter, and may have holes in it along its length, including at the bottom, as in some or all other embodiments herein.

As shown, the separation unit may be fixed to the support unit, and the mix unit may be attached to the bearing. The bearing may be fixed to one or both of the support unit and the separation unit.

The mix unit 702 may include a two stage channel formed with an upper space 702A for receiving the bearing 706, and a lower space 702B that is formed for receiving the filter unit 704. The lower space 702B may have a larger diameter than the upper space 702A, and the upper space may be defined in part by a shoulder section 702C configured to be positioned above the walls of the bearing.

FIG. 8 is an assembled view of components of a mixing and filtering system.

Figure 9:
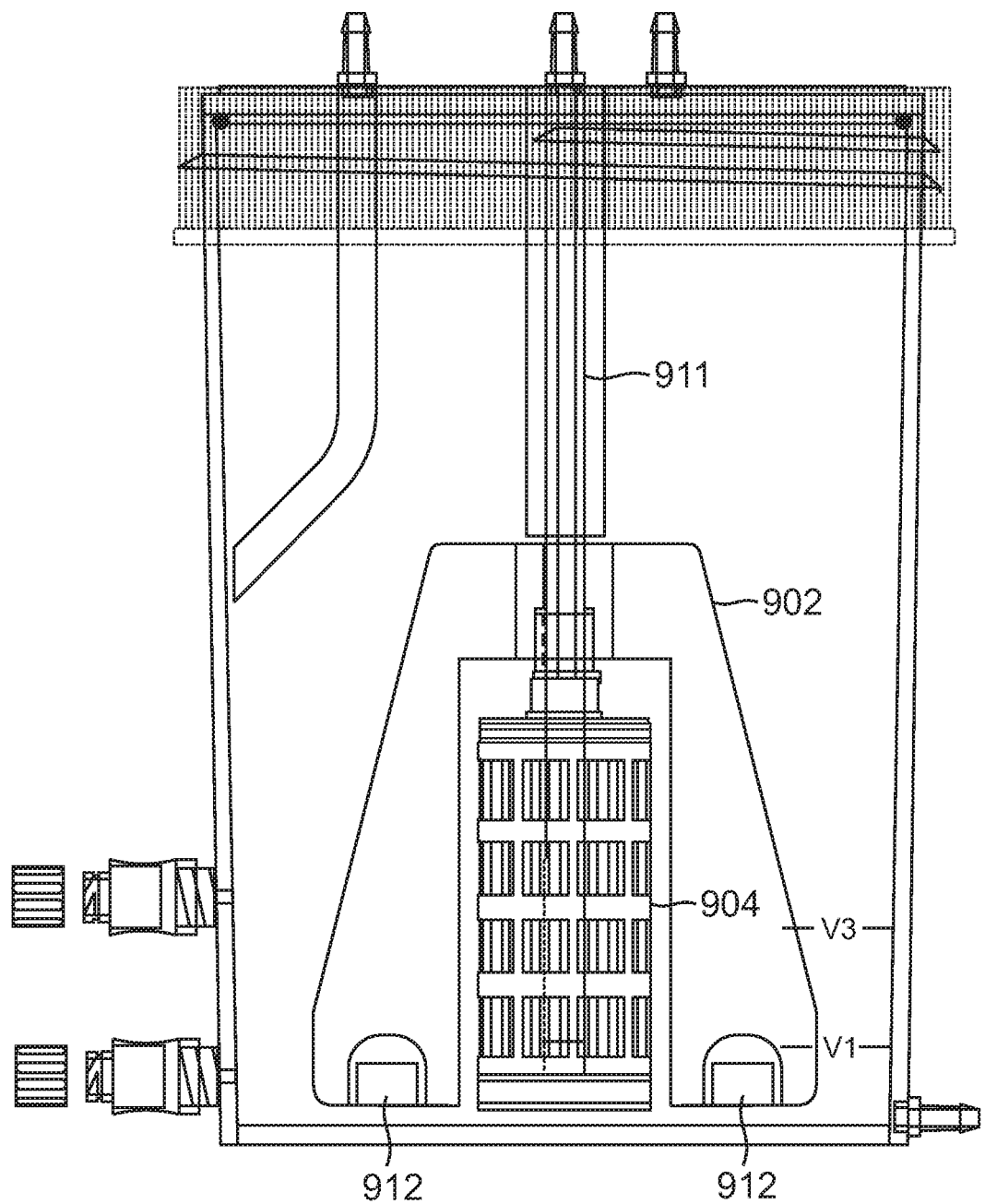
FIGS. 9, 10, and 11 show various additional embodiments of mixing and filtering systems that use similar container arrangements.
Figure 10:
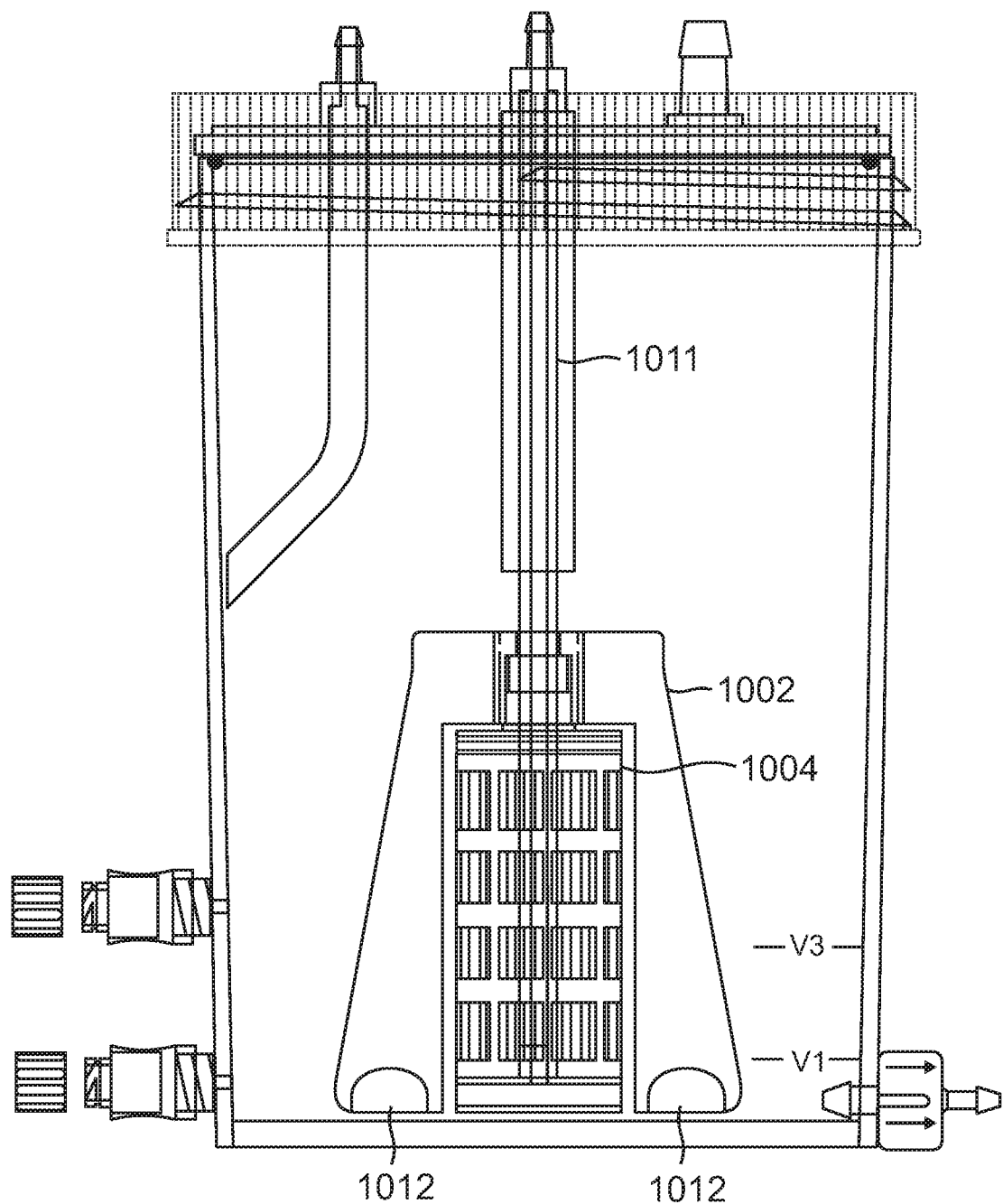
Figure 11:
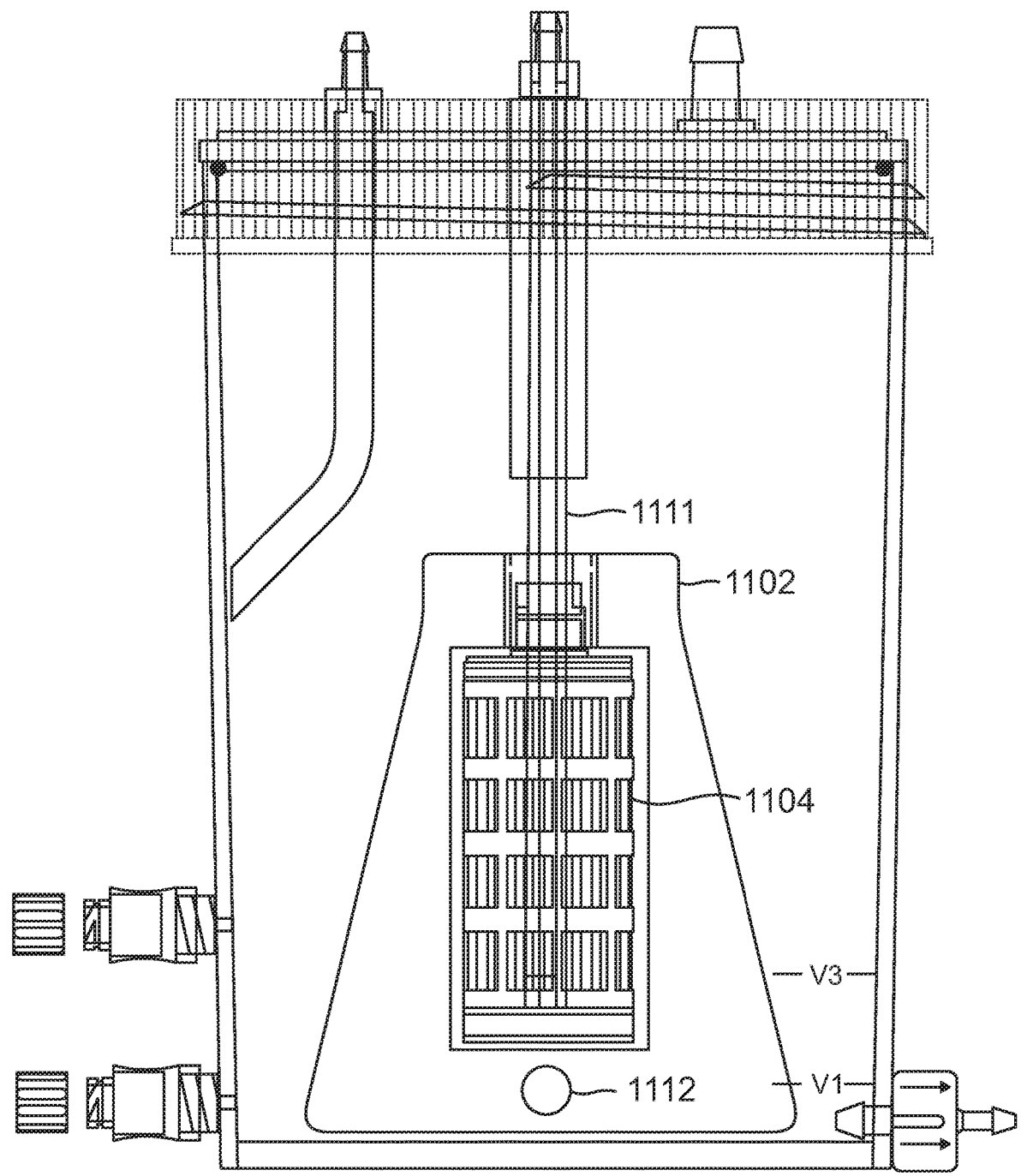

H. FIGS. 9, 10, and 11

FIGS. 9, 10, and 11 show various additional embodiments of mixing and filtering systems that use similar container arrangements.

In these Figures, there are respective vessels, support units 911, 1011, 1111, bearings, mixing units 902, 1002, 1102, filter units 904, 1004, 1104 and magnets 912, 1012, 1112, which operate as in other embodiments herein.

The support units 911, 1011, 1111, like support unit 108, may provide a place for a diptube like diptube 106 inside. The diptube preferably extends down to the bottom of the filter, and may have holes in it along its length, including at the bottom, as in some or all other embodiments herein.

In the various embodiments, the vessels or containers may have various volume markings, such as V1, V2, V3, V4 and V5, as shown in various drawings. They may represent amounts such as 100, 175, 300, 150 and 200 milliliters.

With reference to FIGS. 5A and 5B, one example of how the mixing and filtering systems are used is as follows:

A culture fluid with cells that are to be separated from the fluid is introduced into the aseptic vessel or container 514, e.g., via a bent tube 550. The fluid flows in the direction of arrow A, through the tube, and then down the sidewall of the vessel. Typically the vessel is filled to no more than a height of the top of the filter 504, which may, for example, be 400 to 500 milliliters. The fluid is mixed in the vessel by turning on the magnetic plate just below the vessel (see FIG. 4A for example), which drives the mixing assembly 502 due to magnetic force on magnets 512 located in the bottom of the wings of the mixing assembly. Typical impeller speed is 30 to 100 rpm, so that cells are not damaged.

While mixing is going on, fluid is being drawn through the filter in the general direction of arrow B and into the diptube 506 via its holes, then up the diptube in the direction of arrow C. The filter may keep the larger, i.e., healthier cells in the vessel, while unhealthy or damaged cells and debris which are generally smaller pass through the filter, and go out of the vessel, forming a concentrated mixture of culture and healthy cells in the vessel. In the case of cells being grown on micro carriers, the fluid with the cells and micro carriers is filtered such that the cells, which are smaller than the micro carriers (such as glass beads), are drawn through the filter and up through the diptube.

In other embodiments, fluid flow may be opposite to that shown in FIG. 5A.

Most bearings for the mixing assembly are designed to be in the fluid, so that they are lubricated. In this case, cells can be ground up in the fluid. In preferred embodiments disclosed above, the bearing may be kept above the fluid level, e.g., it may sit in a top of the mixing assembly. (See, e.g., FIGS. 1A, 3A, 5A, 6A, and 8-11. This bearing may be a magnetic bearing in a stainless steel plate or other dry bearing device. Accordingly, the bearing's motion will not damage cells in the culture fluid.

In some or all of the above embodiments, the diptube may have holes at its bottom or proximate its bottom, which bottom portion extends to the bottom of the filter. This arrangement helps the system remove fluid that is located near the bottom of the vessel to help achieve maximum separation and therefore maximum concentration of healthy cells.

In some or all of the above embodiments, the diptube may be located inside the support (co-axially disposed inside) so that the support is out or mostly out of the fluid and provides the support for the filter and for the mixing assembly (the wings).

In the above embodiments of FIGS. 1A, 5A, 6, 8, 9 and 10, the magnets are built into the bottom portion of the wings. This enables the magnets to be close to the bottom of the vessel so that they may be readily driven by the magnetic plate, and at the same time allows the mixing wings to reach as close to the bottom of the vessel as possible. Because the wings are spread and supported above the filter, the filter is also able to extend down as close to the bottom of the vessel as possible. This enables maximum separation of cells into a maximum concentration of cells. Thus, the filter, the magnetic unit (magnets) and the mixing wings may all extend down to the same or substantially the same distance from the vessel bottom. The magnets preferably are arranged so as to have opposite polarities facing downward and thus opposite polarities facing upward.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

It is claimed:

1. A mixing container assembly which can be used to grow and separate cells or micro carriers from liquid or fluid medium in an aseptic environment, comprising:
  a. a container having a sealing mechanism for being sealed both air and liquid tight, the container having a flat bottom;
  b. at least one port through a portion of the container to allow for the introduction of fluid, gas or components;
  c. a central filter fixedly mounted in the container and extending into proximity with the bottom of the container;
  d. a mixing assembly rotatably suspended from above the filter and having fins that rotate around an outer periphery of the filter and extend into proximity with the bottom of the container;
  e. a magnetic unit in a lower portion of the mixing assembly that allows for coupling to a stir plate for driving the fins of the mixing assembly from below the bottom of the container; and
  f. a central diptube which extends from the top of the container through the filter and proximate the bottom of the container.

2. The mixing container assembly of claim 1, wherein the mixing assembly is suspended from above the central filter with an integral bearing device.

3. The mixing container assembly of claim 2, wherein there is a central support which serves as an axis of rotation for the fins and as a support for the integral bearing device.

4. The mixing container assembly of claim 2, wherein the integral bearing device is designed to work dry.

5. The mixing container assembly of claim 2, wherein the integral bearing device is located inside a bore in a top portion of the mixing assembly.

6. The mixing container assembly of claim 1, wherein the mixing assembly is supported by a framework.

7. The mixing container assembly of claim 1, wherein the filter is constructed with filter mesh that is one of pleated and/or flat screen.

8. The mixing container assembly of claim 1, wherein the magnetic unit comprises a split magnet in which there are two magnets oriented in opposing directions and spaced from each other more than a diameter of the filter, whereby the filter is disposed between the magnets.

9. The mixing container assembly of claim 1, wherein the container is a rigid container.

10. The mixing container assembly of claim 1, wherein the mixing assembly fins each extend laterally away from the bottom of the filter at a lower horizontal edge adjacent to the bottom of the container, and a top of each fin is narrower than the lower horizontal edge.

11. The mixing container assembly of claim 1, wherein the mixing assembly does not extend underneath the filter.

12. The mixing container assembly of claim 1, wherein the magnetic unit comprises a dual magnet design with two magnets that are the same size and shape at a low point of the fins of the mixing assembly, with one magnet being located pointing its north pole in the downward position and the other is pointing its opposing south pole in the downward position.

13. A mixing container assembly which can be used to grow and separate cells or micro carriers from liquid or fluid medium in an aseptic environment, comprising:
  a. a container having a sealing mechanism for being sealed both air and liquid tight and having a bottom;
  b. at least one port through a portion of the container to allow for the introduction of fluid, gas or components;
  c. a central filter fixedly mounted in the container and extending into proximity with the bottom of the container;
  d. a mixing assembly rotatably suspended from above the filter and having two fins that rotate around an outer periphery of the filter and extend into proximity with the bottom of the container, the fins each extending laterally away from the bottom of the filter at a lower horizontal edge adjacent to the bottom of the container, and a top of each fin is narrower than the lower horizontal edge;
  e. a magnet in a lower portion of each fin that allows for coupling to a stir plate for driving the fins of the mixing assembly from below the bottom of the container; and
  f. a central diptube which extends from the top of the container through the filter and proximate the bottom of the container.

14. The mixing container assembly of claim 13, wherein the mixing assembly is suspended from above the central filter with an integral bearing device, the assembly having a central support which serves as an axis of rotation for the fins and as a support for the integral bearing device.

15. The mixing container assembly of claim 14, wherein the integral bearing device is designed to work dry and located inside a bore in a top portion of the mixing assembly.

16. The mixing container assembly of claim 13, wherein the filter is constructed with filter mesh that is one of pleated and/or flat screen.

17. The mixing container assembly of claim 13, wherein the magnet in each fin is oriented in an opposing direction from the other magnet and spaced from the other magnet more than a diameter of the filter, whereby the filter is disposed between the magnets.

18. The mixing container assembly of claim 13, wherein the container is a rigid container and the bottom of the container is flat.

19. The mixing container assembly of claim 13, wherein the mixing assembly does not extend underneath the filter.

20. The mixing container assembly of claim 13, wherein the fins are vertically extending and the filter is cylindrical.

* * * * *